United States Patent
Behuria et al.

(10) Patent No.: US 11,837,361 B2
(45) Date of Patent: Dec. 5, 2023

(54) SYSTEM OR METHOD FOR REAL-TIME ANALYSIS OF REMOTE HEALTH DATA AGGREGATED WITH VITAL SIGNS TO PROVIDE REMOTE ASSISTANCE

(71) Applicant: Aetna Inc., Hartford, CT (US)

(72) Inventors: Ajay Behuria, Hartford, CT (US); Alan Bachman, Hartford, CT (US); Vatsamanu Marulachary, Hartford, CT (US); Anthony J. Cevoli, Hartford, CT (US)

(73) Assignee: Aetna Inc., Hartford, CT (US)

(*) Notice: Subject to any disclaimer, the term of this patent is extended or adjusted under 35 U.S.C. 154(b) by 952 days.

(21) Appl. No.: 16/805,194

(22) Filed: Feb. 28, 2020

(65) Prior Publication Data

US 2021/0272690 A1 Sep. 2, 2021

(51) Int. Cl.
| | |
|---|---|
| *G16H 40/67* | (2018.01) |
| *G16H 80/00* | (2018.01) |
| *A61B 5/20* | (2006.01) |
| *A61B 90/00* | (2016.01) |
| *G06N 20/00* | (2019.01) |
| *A61B 5/00* | (2006.01) |

(52) U.S. Cl.
CPC .............. *G16H 40/67* (2018.01); *A61B 5/201* (2013.01); *A61B 5/749* (2013.01); *A61B 90/36* (2016.02); *G06N 20/00* (2019.01); *G16H 80/00* (2018.01); *A61B 2090/365* (2016.02); *A61B 2505/01* (2013.01)

(58) Field of Classification Search
CPC ......... A61B 90/36; A61B 5/201; A61B 5/749; A61B 2505/01; G16H 40/67; G16H 80/00; G06N 20/00
See application file for complete search history.

(56) References Cited

U.S. PATENT DOCUMENTS

| | | | |
|---|---|---|---|
| 11,633,103 B1* | 4/2023 | Nudd ................... | A61B 5/0022 704/9 |
| 2012/0323796 A1* | 12/2012 | Udani .................... | G16H 10/20 705/80 |
| 2012/0323805 A1* | 12/2012 | Udani .................... | G16H 70/20 705/317 |

(Continued)

*Primary Examiner* — Christopher A Flory
(74) *Attorney, Agent, or Firm* — Leydig, Voit & Mayer, Ltd.

(57) ABSTRACT

Methods and systems for analyzing care data are described. The method includes building a virtual model of a physical medical device. Training is provided to a patient associated with the physical medical device to properly use the physical medical device by manipulating the virtual model. First care data associated with a first sensor associated with the physical medical device and second care data associated with a second sensor is received by a cloud service. The cloud service analyzes the first care data to obtain a first care data score and analyzes the second care data to obtain a second care data score. The cloud service scores, using a machine learning algorithm, the first care data score and the second care data score to obtain a combined care score. The cloud service determines whether the combined care score is greater than a threshold. The cloud service triggers an emergency procedure when it is determined that the combined care score is greater than the threshold.

20 Claims, 9 Drawing Sheets

(56) References Cited

U.S. PATENT DOCUMENTS

| | | | | |
|---|---|---|---|---|
| 2016/0354039 A1* | 12/2016 | Soto | ......................... | A61B 5/74 |
| 2018/0001184 A1* | 1/2018 | Tran | ...................... | G16H 50/20 |
| 2019/0065970 A1* | 2/2019 | Bonutti | .................. | A61B 5/021 |
| 2020/0085300 A1* | 3/2020 | Kwatra | ................... | G16H 20/00 |
| 2020/0357299 A1* | 11/2020 | Patel | ......................... | A61B 5/11 |
| 2021/0257093 A1* | 8/2021 | Griffin | ................... | G16H 50/20 |

\* cited by examiner

SYSTEM OR METHOD FOR REAL-TIME ANALYSIS OF REMOTE HEALTH DATA AGGREGATED WITH VITAL SIGNS TO PROVIDE REMOTE ASSISTANCE

BACKGROUND OF THE INVENTION

Individuals increasingly have access to complex medical devices in their homes. These devices can provide life prolonging services to patients. However, the devices can be complex and correct operation is essential to the safety and health of the individuals using them.

Keeping a complex medical device in one's home reduces or eliminates the need to go to doctors' offices, hospitals and other medical provider offices. It is more convenient for individuals to remain in their homes. Additionally, depending on their condition, it may be safer for some individuals to avoid travelling.

In addition to travelling to a medical office, some procedures can take a long time to complete. Individuals will be more comfortable in their own homes while undergoing hours long medical procedures. However, the complexity of various medical devices makes deploying them in individual homes difficult. People must be trained on their correct operation. If an issue arises during the operation of the machine, people must know first that the issue is occurring and second how to correct the issue.

BRIEF SUMMARY OF THE INVENTION

In one embodiment, the invention provides a method for analyzing care data. The method comprises building a virtual model of a physical medical device. Training is provided to a patient associated with the physical medical device to properly use the physical medical device by manipulating the virtual model. First care data associated with a first sensor associated with the physical medical device and second care data associated with a second sensor is received by a cloud service. The cloud service analyzes the first care data to obtain a first care data score and analyzes the second care data to obtain a second care data score. The cloud service scores, using a machine learning algorithm, the first care data score and the second care data score to obtain a combined care score. The cloud service determines whether the combined care score is greater than a threshold. The cloud service triggers an emergency procedure when it is determined that the combined care score is greater than the threshold.

In another embodiment, a non-transitory computer readable medium storing instructions, that when executed by a processor, cause the processor to perform steps is provided. The steps comprise building a virtual model of a physical medical device. Training is provided to a patient associated with the physical medical device to properly use the physical medical device by manipulating the virtual model. First care data associated with a first sensor associated with the physical medical device and second care data associated with a second sensor is received by a cloud service. The first care data is analyzed to obtain a first care data score and the second care data is analyzed to obtain a second care data score. The first care data score and the second care data score are scored, using a machine learning algorithm, to obtain a combined care score. It is determined whether the combined care score is greater than a threshold. An emergency procedure is triggered when it is determined that the combined care score is greater than the threshold.

In yet another embodiment, a device for analyzing care data is provided. The devices comprises a processor and a non-transitory computer readable medium storing instructions, that when executed by the processor, cause the processor to perform steps comprising building a virtual model of a physical medical device. Training is provided to a patient associated with the physical medical device to properly use the physical medical device by manipulating the virtual model. First care data associated with a first sensor associated with the physical medical device and second care data associated with a second sensor is received by a cloud service. The first care data is analyzed to obtain a first care data score and the second care data is analyzed to obtain a second care data score. The first care data score and the second care data score are scored, using a machine learning algorithm, to obtain a combined care score. It is determined whether the combined care score is greater than a threshold. An emergency procedure is triggered when it is determined that the combined care score is greater than the threshold.

DETAILED DESCRIPTION OF THE INVENTION

Sensors are increasingly used for monitoring and providing details about a state of the environment and the health of individuals. Sensors can be deployed in vehicles, homes, offices, and other locations. Sensors can also be deployed on individuals and even embedded in individuals. Sensors are also embedded in physical medical devices. For example, a hemodialysis machine has numerous sensors associated with it. Embodiments described herein provide time sensitive and responsive healthcare management by leveraging healthcare sensors and actuators.

In some embodiments, sensor data is gathered from a physical medical device and a patient using the physical medical device. The data is transmitted to a cloud computing service. The cloud service may use artificial intelligence algorithms to analyze the data. If an issue is detected with the machine, its operation by the patient, or the patient, an emergency procedure, such as alerting a medical professional, is performed. In some embodiments, the medical professional can view a virtual model of the medical device. The virtual model can be updated in real-time to show the current state of the medical device. In this way, the medical professional can give the patient instructions to correct an issue with the machine and see the correction being made in real-time in the virtual model.

Additionally, the patient can be trained to properly use the medical device. The training can occur in person or can occur remotely. Using the virtual model, a medical professional can view the operation of the device in real time and provide training to the patient. This and other embodiments will be described in more detail with respect to the figures.

Figure 1:
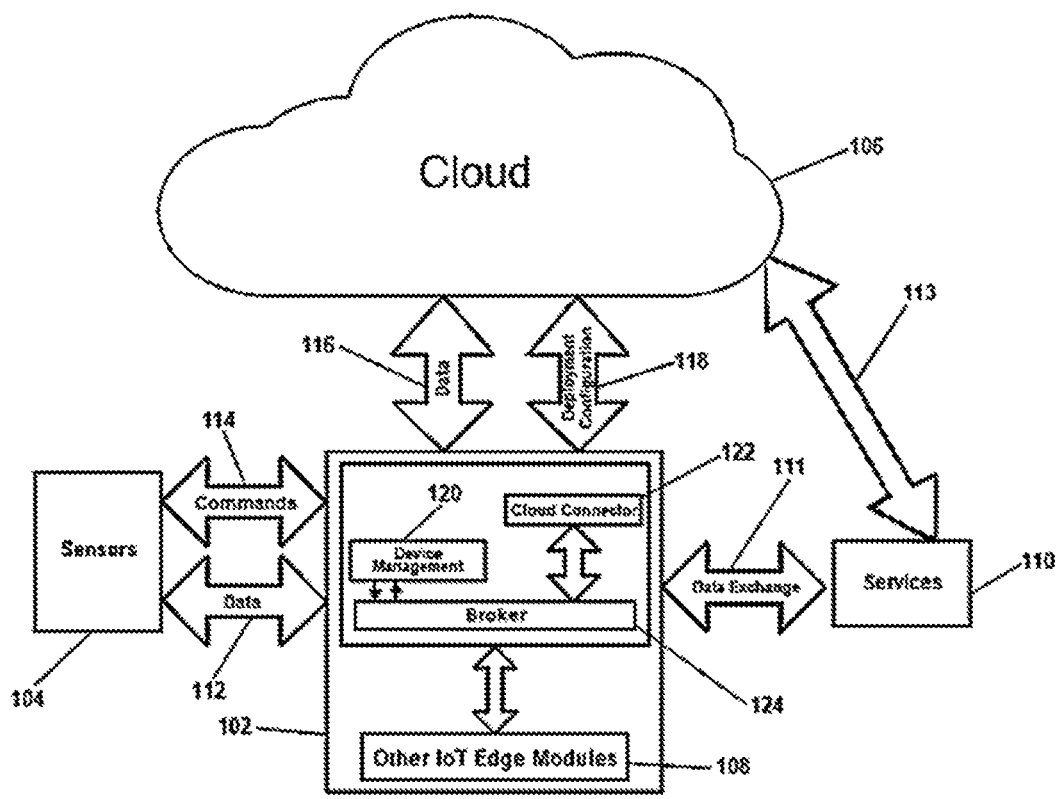
FIG. 1 illustrates a system diagram of a computing environment for analysis of remote health data according to an embodiment.

Turning to the figures, FIG. 1 illustrates a system diagram of computing environment for analysis of remote health data according to an embodiment. In this embodiment, an edge computing device 102 connects to sensors 104 and cloud computing resources 106. The cloud computing resources 106 include cloud services. Sensors 104 can include one or more sensors for collecting physical medical device data, environmental data or data from an individual. Example physical medical devices include a hemodialysis machine, cardiac and pulmonary assist devices with sensors, and machines that provide infusion services, pacemakers with sensors, automated external defibrillators, implantable cardioverter defibrillators, blood gas analyzers, PACS systems, CT scanners, MRI scanners, and others. The physical medical devices can be located anywhere appropriate, including at, for example, a patient's home, medical office or hospital. Sensors on the physical medical device may include sensors regarding the machine's interface and position of knobs and switches. Sensors may also monitor the operating conditions of the machine and include temperature sensors, pressure sensors and others. Example sensors for collecting data from an individual include a heart rate monitor, temperature sensor, smart ring, smart glasses, a smart shirt, a smart watch, Bluetooth tracker, smart shoes, smart socks, smart pants, a smart belt, an Simultaneous GPS (SGPS)/General Packet Radio Service (GRPS) baby control, a smart bracelet, and a smart finger. A smart finger may be a wearable device, or a device implanted in the user. For example, the wearable or implanted device may continuously measure how a person's fingernail bends and moves, which is an indicator of grip strength. Grip strength is a useful metric in a broad set of health issues. It has been associated with the effectiveness of medication in individuals with Parkinson's disease, the degree of cognitive function in schizophrenics, the state of an individual's cardiovascular health, and all-cause mortality in geriatrics.

Environmental sensors may include air quality sensors, smoke detectors, and temperature sensors. The sensors can gather various pieces of data including heart rate, body temperature, movement, geographic location, elevation, step count, number of stairs climbed, blood oxygen level, and more.

In some embodiments, edge computing device 102 can send and receive data from sensors 104 through data channel 112. Edge computing device 102 can also send and receive commands from sensors 104 through command channel 114. The edge computing device 102 communicates with sensors using any appropriate network connection, such as Bluetooth, Wi-Fi, cellular and others. In these embodiments, the edge computing device 102 may act as a gateway device connecting the various sensors to the cloud 106.

In some embodiments, edge computing device 102 interfaces with various internet of things (IOT) modules through connection 108. Example IoT modules at the edge include modules to deidentify patient data prior to sending it to the cloud. Patient data may be deidentified for privacy and security reasons. Additional examples include modules for data aggregation from multiple sensors, modules for data filtration, and modules for synchronous/asynchronous messaging between the modules at the edge computing device.

Additionally, in some embodiments, the edge computing device 102 may interface with various emergency and non-emergency services 110 though a data exchange 111. These service 110 may include a traffic management center, a pharmacy, a electronic health record, an electronic medical record, emergency services such as police, fire and medical personal, paramedics, emergency care providers and health insurers. Other services 110 may include informational services such as weather services. The edge computing device 102 can both send and receive data from the services using various cellular, Wi-Fi and other networks.

Edge computing device 102 also interfaces with cloud computing resources 106. The cloud computing resources may include third party resources or may be hosted by the entity providing the edge computing device 102. Additionally, cloud computing resources 106 may also be a computing device owned or controlled by the individual the is using the edge computing device.

The edge computing device 102 can send and receive data from the cloud computing resources 106 through data channel 116. Edge computing device 102 can also send and receive commands and deployment configuration information through channel 118. Device management at the edge requires providing configuration information, updates and patches to the edge device. The deployment configuration information is referring to these types of device management related instructions and payloads. For example, an edge computing device and sensors may be provided to a user. Deployment configuration information may be used to provide the initial configuration for the edge computing device and sensors.

The edge computing device 102 can be worn by an individual, carried by an individual, or installed at a location. For example, the edge computing device could be a mobile computing device, such as a mobile phone or tablet computer worn by an individual. In some embodiments, the edge computing device 102 may be a wearable computer, such as a high power smart watch. In other embodiments, the edge computing device may be a computer, router or media device at an individual's home or work. Any computing device with appropriate processing power and network connectivity could be the edge computing device.

The edge computing device 102 includes a number of software and hardware modules for connectivity and processing. For example edge computing device 102 may include a device management module 120. The device management module 120 interfaces with the various sensors 104 that are connected to or may connect to the edge computing device 102. The device management module 120 may monitor and track sensor state, and provide a rule engine for processing and scoring data from the sensors. This process is described below.

The edge computing device 102 also includes a cloud connector 122. The cloud connector 122 connects to the various public and private cloud computing resources 106. A broker 124 interfaces the device management module 120, the cloud connector 122 and the other IoT modules through connection 108 together. In this embodiment, data and commands to and from the sensors 104 is sent through the device management module 120, data and commands to and from the cloud computing resources 106 is sent through the cloud connector 122.

In some embodiments the edge computing device is not always or always expected to be connected to the cloud computing resources through the network. In such cases, the edge computing device, such as a mobile computing device will intermediately connect to the cloud computing resources and exchange data when connected. For example, mobile computing device may connect to the network using a cellular connection.

Figure 2:
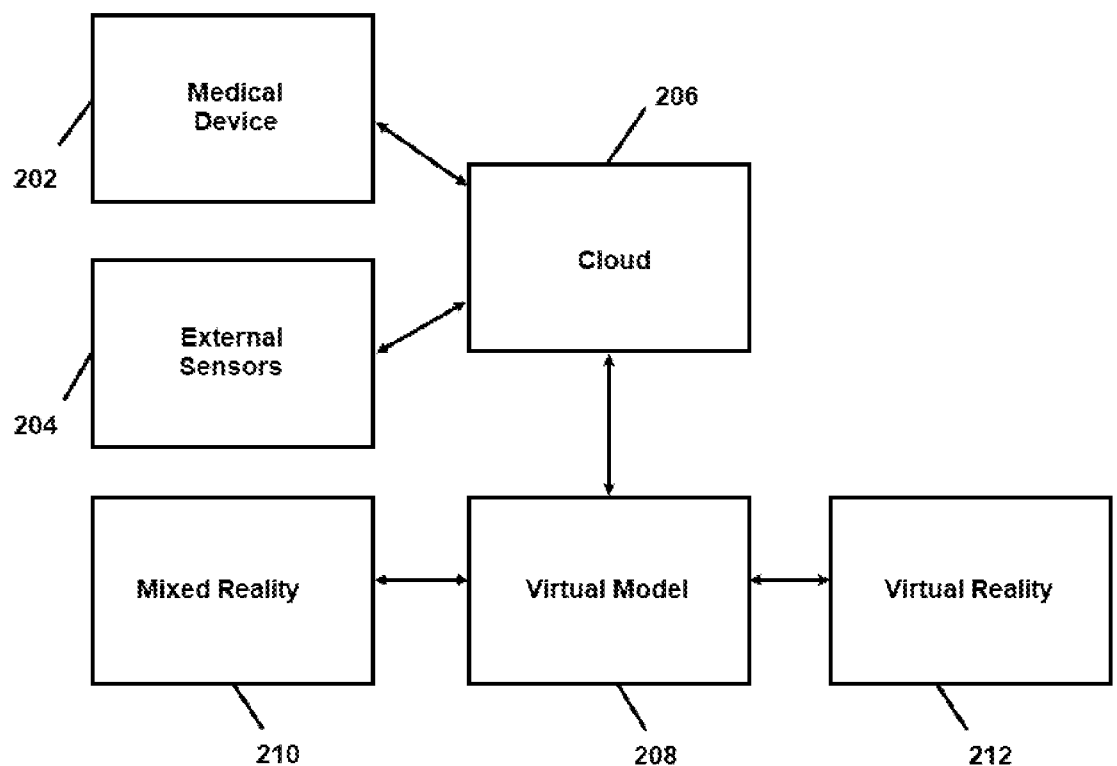
FIG. 2 illustrates components of a computing environment for analysis of remote health data according to an embodiment.

In some embodiments, the medical device and other sensors may connect directly to the cloud computing resources without using the edge computing device as a gateway. FIG. 2 illustrates components of a computing environment for analysis of remote health data according to an embodiment. As illustrated the physical medical device 202 and external sensors 204 connect directly to the cloud computing services 206. The cloud services 206 can build a virtual model 208 of the medical device 202. Building a virtual model can include creating a model, configuring a model a model already provided and/or instantiating a model. The virtual model 208 can be used for augmented reality/mixed reality 210 viewing or virtual reality viewing 212. Additionally, the virtual model can be used by the cloud services 206 to power interactive artificial intelligence, such as a voice assistant. The cloud services 206 can transmit services to support augmented reality, virtual reality, voice assistants and other interfaces.

For example, in one embodiment the cloud service 206 builds a virtual model 208 of a physical medical device 202. Training is provided to a patient associated with the physical medical device 202. For example, a medical professional may provide training using the virtual model. The patient may use a mixed reality device 210 to view instructions, machine settings and other parameters overlaid with the physical medical device 202. The physical medical device 202 can send, to the cloud service 206, care data associated with a first sensor in the physical medical device 202. Additionally, care data can be sent from the external sensors 204 to the cloud service 206. The external sensors 204 can include, for example, sensors associated with the patient, such as a heart rate monitor or temperature sensor.

The cloud service 206 can then analyze the care data and obtain a first care data score for the medical device 202 care data and a second care data score for the external sensor 204 care data. The cloud service 206 the scores, using a machine learning algorithm, the first care data score and the second care data score to obtain a combined care score. The cloud service 206 determines whether the combined care score is greater than a threshold. If the combined care score is greater than the threshold, the cloud service triggers an emergency procedure. The emergency procedure could include contacting emergency medical services. It could also display the virtual model 208 on a graphical display or a virtual reality headset 212. In this way, a medical professional can view changes to the physical medical device in real-time and provide instructions over a phone or other means to the patient. The emergency procedure can include automatically contacting a medical professional.

Figure 3:
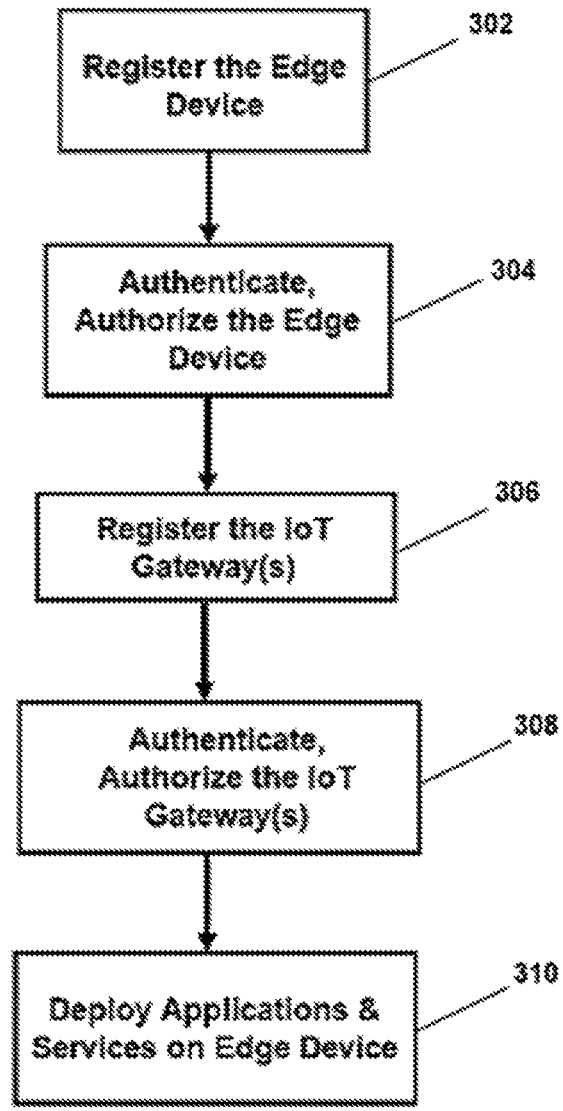
FIG. 3 is a flow diagram of a method for configuring an edge computing device according to an embodiment.

FIG. 3 is a flow diagram of a method for configuring an edge computing device according to an embodiment. This flow can be used in embodiments that use an edge device. As noted above, in some embodiments an edge device is not used. At step 302, the edge device is registered. Step 302 may include registering the edge computing device with the cloud computing resources. At step 304, the edge computing device is authenticated, and the edge computing device is authorized. For example, organization identification, device type, device identification, and an authentication token may be provided to configure the edge device and connect to the cloud computing resources. At step 306, any gateways, such as IoT gateways are registered. The gateways are managed devices to that may connect to an IoT platform, such as cloud computing resources. In one embodiment, the gateway is the edge computing device or a component in the edge computing device, such as the cloud connector 302 in FIG. 1. In this embodiment, the gateway is registered at the time the edge computing device is registered in step 302.

At step 308, the gateway device is authenticated, and the gateway device is authorized. For example, organization identification, device type, device identification, and an authentication token may be provided to configure the edge device and connect to the cloud computing resources. In one embodiment, the gateway is the edge computing device or a component in the edge computing device, such as the cloud connector 202 in FIG. 1. In this embodiment, the gateway is registered at the time the edge computing device is registered in step 304. At step 310, applications and services are deployed on the edge computing device. The applications and services may be implemented on the edge device using native code or may be implemented in container packages, such as a docker container or KubeEdge. The applications and services maybe used to obtain the sensor data.

While in the embodiments described above, the sensor data and care data is analyzed in the cloud services. In some embodiments, the edge computing device may analyze the care data. The applications and services deployed on the edge computing device may be responsible for all or a portion of its functionality. Example functionality includes connecting to sensors, analyzing sensor data, connecting to cloud services and contacting emergency service providers. Additionally, when sending data to the cloud services, the edge device, or other devices if an edge device is not used, may remove any sensitive information, such as personally identifiable information before sending the care data to the cloud services.

Figure 4:
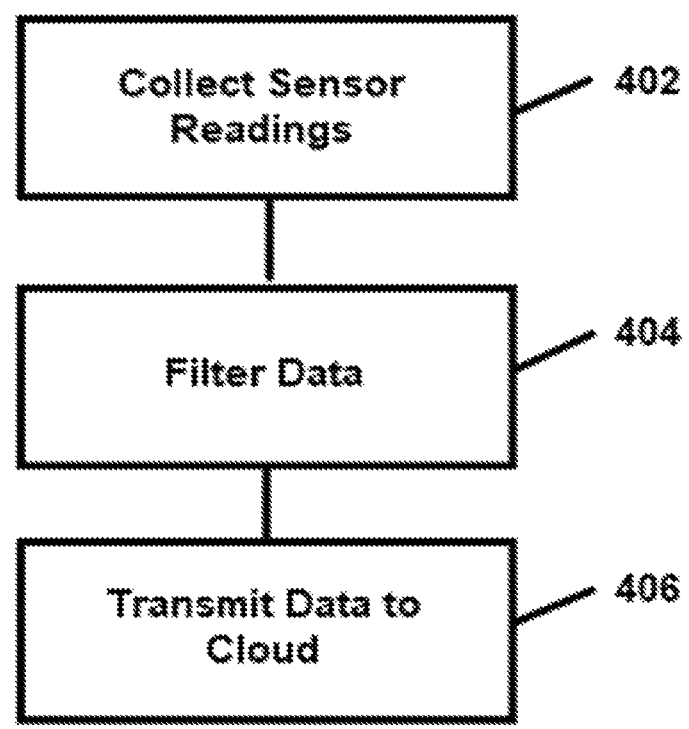
FIG. 4 is a flow diagram of a method for gathering sensor readings according to an embodiment.

FIG. 4 is a flow diagram of a method for gathering sensor readings according to an embodiment. At step 402, the sensors publish information and data to the edge computing device. For example, at step 402, the edge computing device may receive first care data from a first sensor and second care data from a second sensor. At step 406, the sensor data filtered to remove sensitive data, such as personally identifiable information. In this way, data can safely be sent to the could without compromising the privacy of the patient. At step 406, the data is transmitted to the cloud services. While this embodiment is described in the context of an edge computing device, in other embodiments, these steps are performed by the physical medical device or another device.

Figure 5:
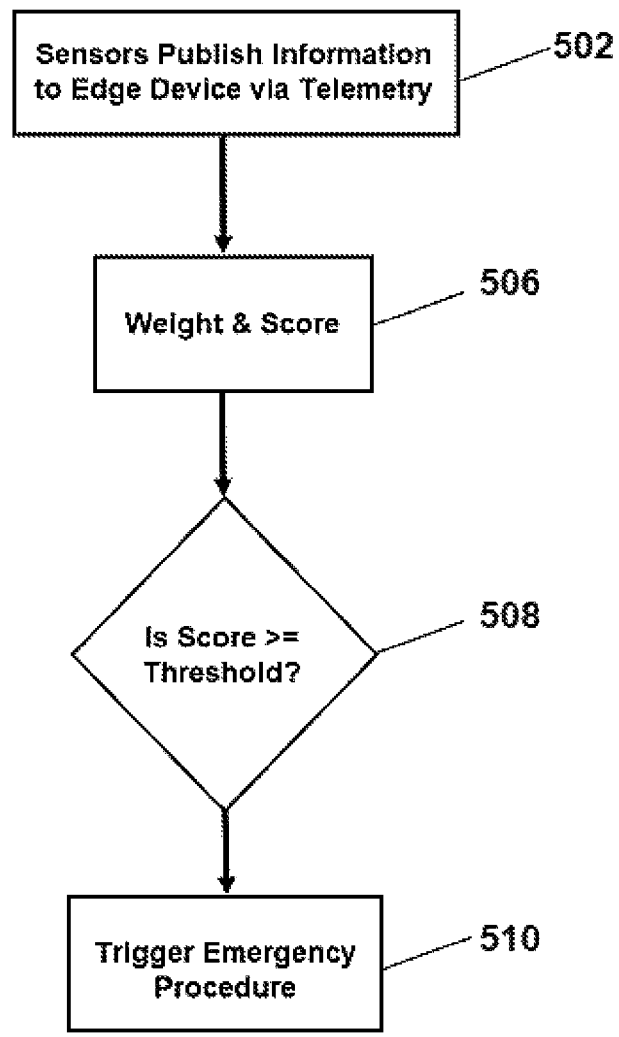
FIG. 5 is a flow diagram of a method for analyzing sensor data according to an embodiment.

FIG. 5 is a flow diagram of a method for analyzing sensor data according to an embodiment. At step 502, the sensors publish information and data to the edge computing device. For example, at step 502, the edge computing device may receive first care data from a first sensor and second care data from a second sensor. In other embodiments, the information may be published to the physical medical device or another device. The information is then sent to the cloud services as described with respect to FIG. 4 above.

At step 506, the sensor data is weighted and scored. For example, at step 506, the cloud services may analyze the first care data to obtain a first care data score. Further, the cloud services may analyze the second care data to obtain a second care data score. In some embodiments, the cloud services, using the machine learning algorithm, analyzes the first care data score and the second care data score to obtain a combined care score. For example, the scores could be added together, averaged, or other appropriate means used to create the combined care score. In some cases, one high care score will result in a high combined care score.

At step 508, the cloud services determine whether the combined score is equal to or exceeds a threshold. In another embodiment, the edge computing device determines whether the combined care score is greater than a threshold. At step 510, an emergency procedure is triggered if the score is equal to or exceeds a threshold. For example, the cloud services may trigger an emergency procedure when it is determined that the combined care score is greater than the threshold. In some embodiments, an emergency procedure includes automatically contacting an emergency service provider. In other embodiments, a care provider or other person is first contacted to determine whether an emergency service provider should be contacted.

Figure 6:
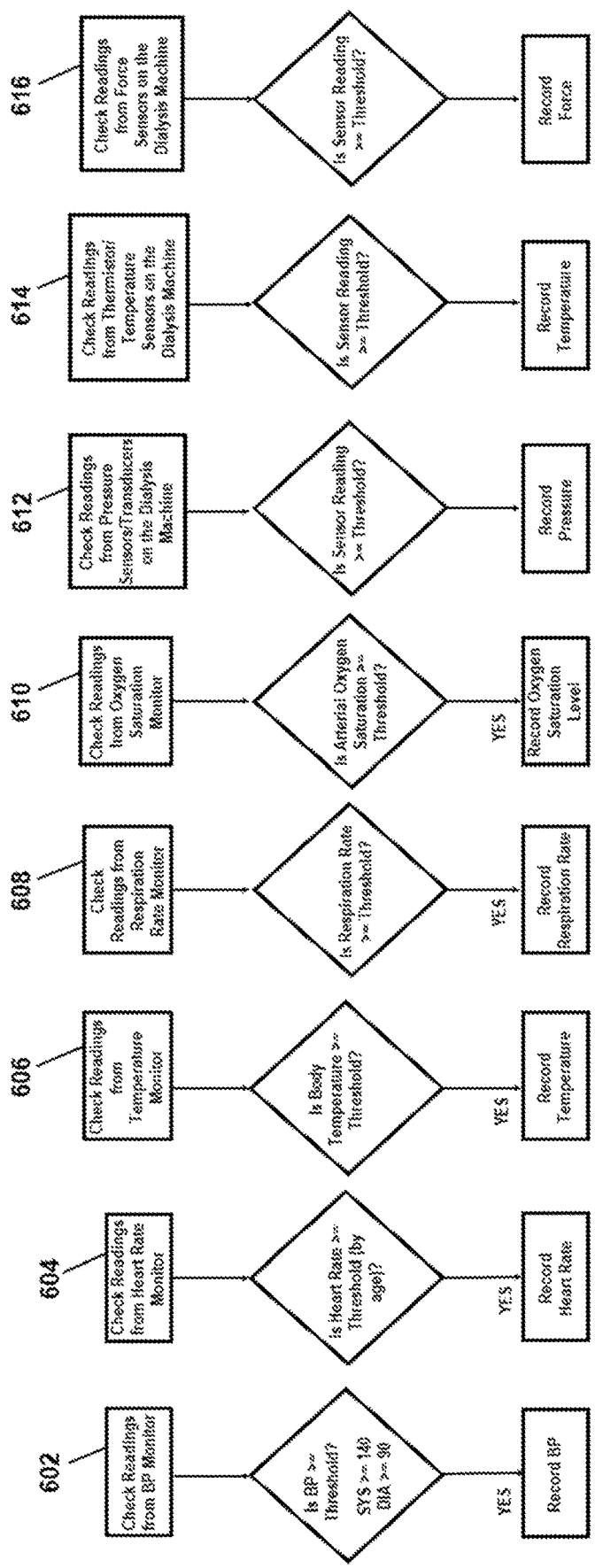
FIG. 6 is a flow diagram illustrating a process for scoring data from various sensors according to an embodiment.

FIG. 6 is a flow diagram illustrating a process for scoring data and determining if the score is greater than a threshold from various sensors according to an embodiment. For example, after the edge computing device receives data from a sensor, it can score the data immediately, or it can send the data to the cloud services for scoring, as described above. At process 602, readings from a blood pressure monitor are analyzed. If the blood pressure exceeds a threshold, the blood pressure reading is recorded by the edge computing device. The blood pressure monitor may be a sensor worn by the patient.

At process 604, readings from a heart rate monitor are analyzed. In one embodiment, an activity tracker includes the heart rate monitor. If the heart rate exceeds a threshold, the heart rate reading is recorded by the edge computing device. Alternatively, if the heart rate exceeds a threshold, the edge computing device determines if the resting heart rate variability exceeds a threshold. If the heart rate variability exceeds a threshold, then the heart rate and heart rate variability are recorded.

At process 606, readings from a temperature monitor are checked. The temperature monitor could be worn by the patient to monitor the patient's temperature. If the temperature exceeds a threshold, the temperature is recorded. At process 608, readings from a respiration rate monitor are checked. If the respiration rate exceeds a threshold, the respiration rate is recorded. At process 610, readings from an oxygen saturation monitor are checked. In one embodiment, if the arterial oxygen saturation is greater than a threshold, then the oxygen saturation level is recorded.

In the illustrated embodiment, a dialysis machine and associated sensors are used. At process 612, readings from pressure sensors and transducers on the dialysis machine are checked. If the sensor reading is greater than a threshold, the pressure is recorded. At process 614, readings from a temperature sensor, such as a thermistor, on the dialysis machine are checked. If the temperature reading is greater than a threshold, than the temperature is recorded. At process 616, readings from force sensors on the dialysis machine are checked. If the force sensors are greater than a threshold, then the force readings are recorded.

While the above sensor readings and processes relate to a dialysis machine, other embodiments incorporate other physical medical devices. In this embodiment, the sensors readings are directly compared to a threshold, thus the sensor reading itself is the score. In other embodiments, the sensor readings may be translated to another scale or system for scoring. For example, the sensor readings could all be translated to a 0-100 scale.

Figure 7:
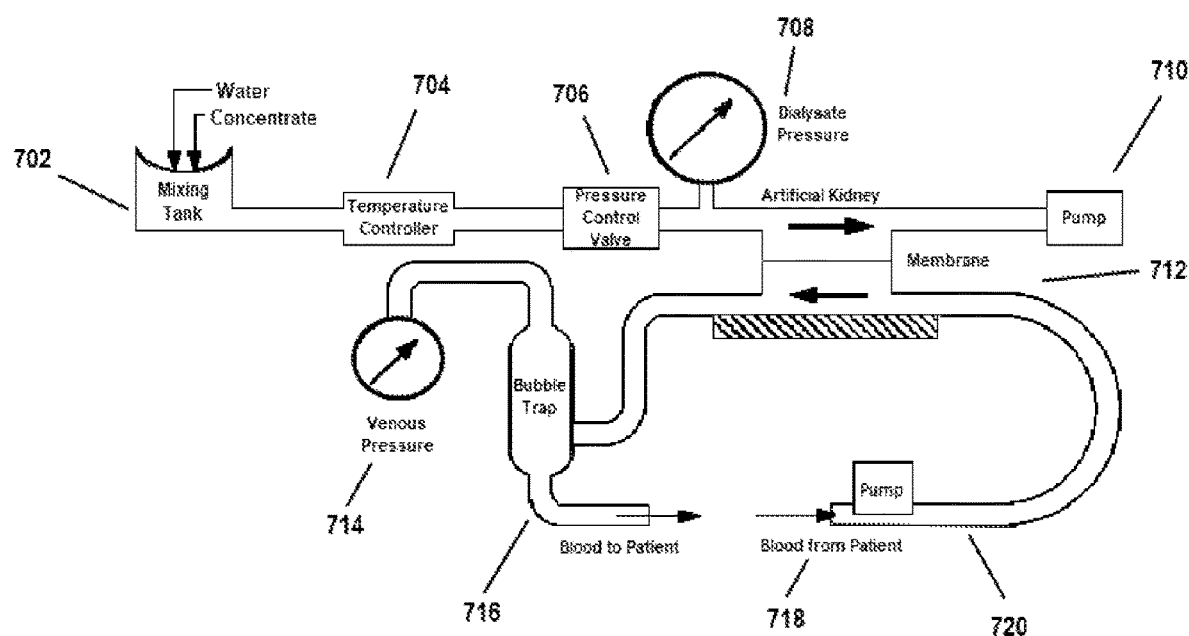
FIG. 7 is a system diagram of a hemodialysis machine according to an embodiment.

FIG. 7 illustrates a system diagram of a hemodialysis machine according to an embodiment. In general, a hemodialysis machine removes waste, toxins and other substances from the blood of a patient whose kidneys no longer work properly. In one example system, at 702, a mixing tank mixes water and dialysis solution concentrate to form dialysis solution in the dialysis machine. A temperature controller 704 brings the dialysis solution to the correct temperature. A pressure controller valve 706 brings the dialysis solution to the correct temperature. A dialysate pressure sensor 708 is used to monitor the pressure in the dialysis machine. A pump 710 pumps the dialysis solution.

A membrane 712 allows material to move from a patient's blood to the dialysis solution. A pressure sensor 714 is used to monitor the venous pressure of the patient. A bubble trap 716 removes any air that was introduced into the blood. At 718, the dialysis machine is connected to the patient and cleaned blood is returned to the patient. At 720 the dialysis machine is connected to the patient and dirty blood is removed from the patient.

Figure 8:
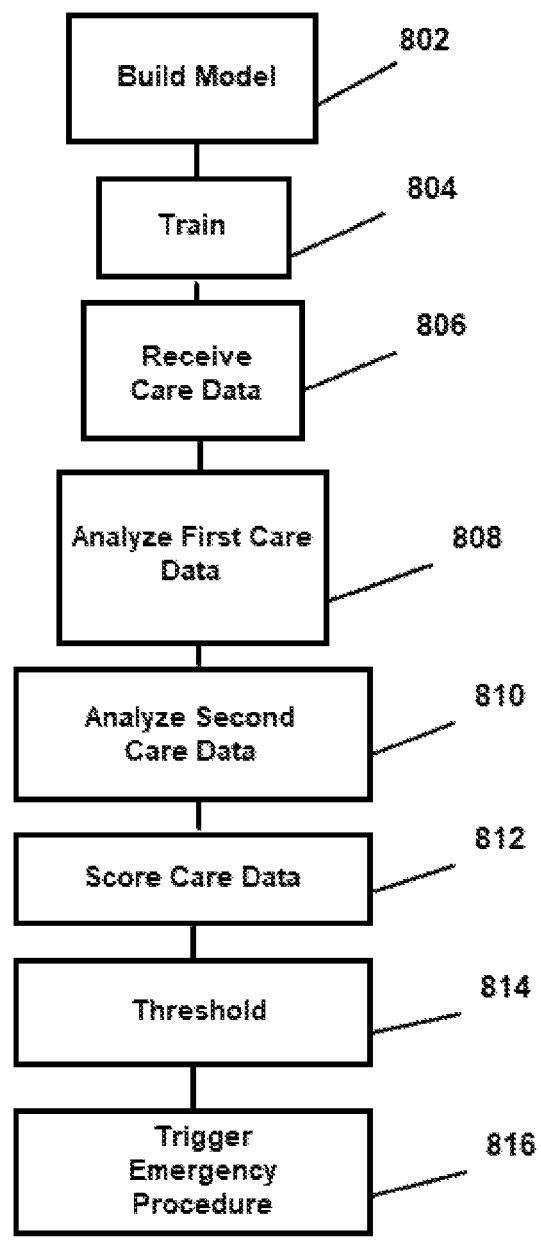
FIG. 8 is a flow diagram illustrating a process for analysis of remote health data according to an embodiment.

FIG. 8 is a flow diagram illustrating a process for analysis of remote health data according to an embodiment. At step 802 a virtual model of a physical medical device is built. The model can be created in advance by, for example, the physical medical device manufacturer. The model can then be instantiated and/or configured by the cloud services. Any combination or creating, configuring and/or instantiating is considered building the model.

At 804, training is provided to a patient associated with the physical medical device to properly use the physical medical device by manipulating the virtual model. For example, a medical professional can use the physical model to show the patient how to use the physical device. The patient may view the model, for example, on a graphical display, in a mixed reality headset or in a virtual reality headset. In some embodiments, the medical professional can manipulate the physical medical device by manipulating the virtual model. For example, the medical professional can change settings and positions of knobs and switches and the physical device will change corresponding settings and positions of knobs and switches. The cloud can transmit the changes to the virtual model to the physical device and changes to the physical device to the virtual model.

At step 806 first care data associated with a first sensor associated with the physical medical device and second care data associated with a second sensor are received by the cloud. The first care data may be the sensor reading or may be data that has been normalized, scored or manipulated in some other way.

At 808 the cloud service analyzes the first care data to obtain a first care data score and at 810 the cloud service analyzes the second care data to obtain a second care data score. At 812, the cloud service scores, using a machine learning algorithm, the first care data score and the second care data score to obtain a combined care score. At 814 cloud service determines whether the combined care score is greater than a threshold. At step 816 when it is determined that the combined care score is greater than the threshold the cloud service triggers an emergency procedure.

Figure 9:
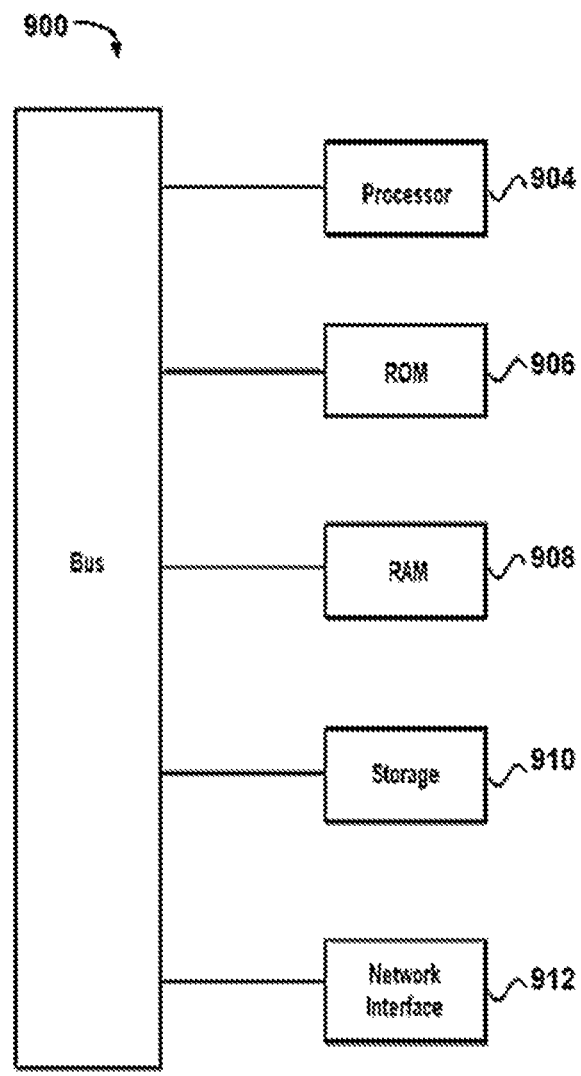
FIG. 9 illustrates a computing device according to an embodiment.

FIG. 9 illustrates a computing device according to an embodiment. The computing device 900 can be used to implement the sensors, physical medical device, edge computing device, cloud computing resources and other devices described above. The computing device 900 includes a processor 904, such as a central processing unit (CPU), executes computer executable instructions comprising embodiments of the system for performing the functions and methods described above. In embodiments, the computer executable instructions are locally stored and accessed from a non-transitory computer readable medium, such as storage 910, which may be a hard drive or flash drive. Read Only Memory (ROM) 906 includes computer executable instructions for initializing the processor 704, while the random-access memory (RAM) 908 is the main memory for loading and processing instructions executed by the processor 904. The network interface 912 may connect to a wired network, wireless network or cellular network and to a local area network or wide area network, such as the internet.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for analyzing care data, the method comprising:
    building a virtual model of a physical medical device;
    providing training to a patient associated with the physical medical device to properly use the physical medical device by manipulating the virtual model;
    receiving, by a cloud service, first care data associated with a first sensor associated with the physical medical device and second care data associated with a second sensor;
    analyzing, by the cloud service, the first care data to obtain a first care data score;
    analyzing, by the cloud service, the second care data to obtain a second care data score;
    scoring, by the cloud service using a machine learning algorithm, the first care data score and the second care data score to obtain a combined care score;
    determining, by the cloud service, whether the combined care score is greater than a threshold; and
    triggering, by the cloud service, an emergency procedure when it is determined that the combined care score is greater than the threshold.

2. The method of claim 1 further comprising:
    registering, by a cloud service, an edge computing device;
    connecting the edge computing device to a cloud service;
    receiving, by the edge computing device, the first care data from the first sensor associated with the physical medical device and second care data from the second sensor;
    filtering, by the edge computing device, sensitive information from the first care data and the second care data.

3. The method of claim 1, further comprising displaying the virtual model on a graphical display, wherein the virtual model shows changes to the physical medical device in real-time.

4. The method of claim 3, wherein the displaying is performed in response to triggering the emergency procedure.

5. The method of claim 4, wherein the graphical display is associated with a medical professional.

6. The method of claim 5 further comprising transmitting instructions from the medical professional to the patient associated with the physical medical device.

7. The method of claim 5 further comprising manipulating the physical medical device by manipulating the virtual model.

8. The method of claim 1, wherein the physical medical device provides at least one of kidney care and infusion services.

9. The method of claim 1, wherein the virtual model is one of an augmented reality and a virtual reality model.

10. The method of claim 1, further comprising transmitting, form the cloud service, a service for providing mixed reality to a patient device associated with the patient.

11. The method of claim 1, further comprising initiating a voice service for interacting with a patient associated with the physical medical device.

12. The method of claim 1, wherein the triggering an emergency procedure comprises automatically contacting a medical professional.

13. A non-transitory computer readable medium storing instructions, that when executed by a processor, cause the processor to perform steps comprising:
    building a virtual model of a physical medical device;
    providing training to a patient associated with the physical medical device to properly use the physical medical device in response to manipulation of the virtual model;
    receiving first care data associated with a first sensor associated with the physical medical device and second care data associated with a second sensor to the cloud service;
    analyzing the first care data to obtain a first care data score;
    analyzing the second care data to obtain a second care data score;

scoring, using a machine learning algorithm, the first care data score and the second care data score to obtain a combined care score;

determining whether the combined care score is greater than a threshold; and triggering an emergency procedure when it is determined that the combined care score is greater than the threshold.

14. The steps of claim 13, further comprising displaying the virtual model on a graphical display, wherein the virtual model shows changes to the physical medical device in real-time.

15. The method of claim 14, wherein the displaying is performed in response to triggering the emergency procedure.

16. The method of claim 14, wherein the graphical display is associated with a medical professional.

17. The method of claim 16 further comprising transmitting instructions from the medical professional to the patient associated with the physical medical device.

18. The method of claim 14 further comprising manipulating the physical medical device by manipulating the virtual model.

19. A device for analyzing care data comprising:

a processor; and a non-transitory computer readable medium storing instructions, that when executed by the processor, cause the processor to perform steps comprising:

building a virtual model of a physical medical device;

providing training to a patient associated with the physical medical device to properly use the physical medical device in response to manipulation of the virtual model;

receiving first care data associated with a first sensor associated with the physical medical device and second care data associated with a second sensor to the cloud service;

analyzing the first care data to obtain a first care data score;

analyzing the second care data to obtain a second care data score;

scoring, using a machine learning algorithm, the first care data score and the second care data score to obtain a combined care score;

determining whether the combined care score is greater than a threshold; and triggering an emergency procedure when it is determined that the combined care score is greater than the threshold.

20. The steps of claim 19, further comprising displaying the virtual model on a graphical display, wherein the virtual model shows changes to the physical medical device in real-time.

* * * * *